United States Patent
St. Lewis et al.

(10) Patent No.: US 6,306,806 B1
(45) Date of Patent: Oct. 23, 2001

(54) DUAL CHAMBER CLEANSING SYSTEM COMPRISING WATER-IN-OIL EMULSION AS BENEFIT STRIPE

(75) Inventors: Dale St. Lewis, Huntington Station, NY (US); Helen Elizabeth Knaggs, Weehawken, NJ (US)

(73) Assignee: Unilever Home & Personal Care USA, Division of Conopco, Inc, Greenwich, CT (US)

( * ) Notice: Subject to any disclaimer, the term of this patent is extended or adjusted under 35 U.S.C. 154(b) by 0 days.

(21) Appl. No.: 09/532,700

(22) Filed: Mar. 22, 2000

(51) Int. Cl.$^7$ ................. C11D 3/18; C11D 3/48
(52) U.S. Cl. ............ 510/159; 510/130; 510/140; 510/406; 510/417; 222/136
(58) Field of Search ................. 510/122, 123, 510/124, 130, 131, 136, 140, 152, 158, 159, 406, 417; 424/401, 450, 452, 78.03; 222/1, 135, 136, 137

(56) References Cited

U.S. PATENT DOCUMENTS 5,455,035 * 10/1995 Guerero et al. .
5,612,307    3/1997 Chambers et al. .
6,150,312 * 11/2000 Puvvada et al. .

* cited by examiner

*Primary Examiner*—Yogendra N. Gupta
*Assistant Examiner*—Gregory E. Webb
(74) *Attorney, Agent, or Firm*—Ronald A. Koatz

(57) ABSTRACT

The invention provides an at least dual compartment container containing at least one surfactant stripe and at least one water-in-oil emulsion stripe. By dispensing a water-in-oil emulsion stripe, greater deposition, particularly deposition of water soluble benefit agent (e.g., glycolic acid) is achieved than believed possible.

14 Claims, No Drawings

DUAL CHAMBER CLEANSING SYSTEM COMPRISING WATER-IN-OIL EMULSION AS BENEFIT STRIPE

FIELD OF THE INVENTION

The present invention relates to a composition for depositing both hydrophilic (e.g., glycolic acid, lactic acid, hydroxy caprylic acid, water soluble vitamins etc.) and hydrophobic (e.g., petrolatum forming the oil part of emulsion) benefit agents in greater amounts than previously possible when using PW shower gel type liquids and/or facial cleansers all while maintaining good foam stability. Specifically, the invention relates to a dual chamber system in which one composition/stripe comprises a surfactant; and a separate composition/stripe, which is co-dispensed, comprises a water in oil emulsion comprising one or more benefit agents. Use of a water-in-oil emulsion rather than an oil in water emulsion as the benefit agent stripe has unexpectedly been found to result in much greater deposition of benefit agent (water soluble benefit agents such as glycolic; non-water soluble benefit agents, and even "semi-soluble" benefit agents solubilized in other components, e.g., salicylic acid solubilized in polyalkylene glycol emulsified in oil).

BACKGROUND OF THE INVENTION

It is greatly desirable to deposit soluble benefit agents (e.g., water soluble benefits such as glycolic acid or lactic acid) and/or hydrophobic agents (e.g., petrolatum) and/or those in between on the skin or other substrate.

However, deposition of benefit agent, particularly water soluble ones, is extremely difficult to accomplish, especially from wash-off type products (e.g., shower gels) because the benefit agent will essentially wash off when the user rinses with water. Although it is easier to deposit a hydrophobic benefit agent (e.g., silicone or petrolatum), rinse-off can still be a problem here as well.

Unexpectedly, applicants have found that, by forming a water-in-oil emulsion of, for example, a water soluble benefit agent in a hydrophobic emulsion and separately dispensing the benefit agent containing emulsion in one stripe and a surfactant containing composition in another, applicants have been able to deposit greater amounts of both the water soluble benefit agent and of the oil forming the emulsion than otherwise achievable (e.g., either through single stripe cleanser or through dual stripe cleanser having only oil in water emulsion rather than water-in-oil emulsion of invention).

The use of separate surfactant and benefit agent stripes is not itself new. U.S. Pat. No. 5,612,307 to Chambers et al., for example, teaches a dual chamber package comprising separate surfactant and benefit agent stripe. The benefit agent in that reference is lipophilic benefit agent only rather than water-soluble benefit agent in oil emulsion. That is, the benefit agent is not in water-in-oil emulsion form such as the benefit agent stripe of the invention.

A multiple emulsion benefit stripe is taught in applicants' copending application entitled "Dual Chamber Cleansing System Comprising Multiple Emulsion" to St. Lewis et al., but this reference does not teach that a water-in-oil benefit stripe in such dual chamber system can provide remarkable deposition relative to, for example, oil-in-water stripe.

BRIEF SUMMARY OF THE INVENTION

Unexpectedly, applicants have found that a dual chamber dispenser comprising a surfactant containing stripe on one side and a water-in-oil emulsion containing benefit stripe on the other (wherein the internal water phase preferably, but not necessarily, contains at least one water soluble benefit agent) is able to deliver both the water soluble benefit agent and the oil which forms the emulsion to the skin or other substrate in greater amounts than otherwise possible, i.e., than if using single stripe or using, for example, an oil in water emulsion as the benefit stripe.

Specifically, the invention comprises:

An aqueous liquid cleansing and moisturizing composition comprising an at least dual chamber dispenser (in theory more than two stripes may be dispensed and the invention is not necessarily limited by the number of stripes) comprising:

(A) 10 to 99.9% by wt., preferably 30 to 99.9%, more preferably 50 to 99.9% of a surfactant containing stripe wherein about 1 to 75%, preferably 5 to 70% of said surfactant stripe comprises a surfactant selected from the group consisting of anionic, nonionic, zwitterionic and cationic surfactants, soap and mixtures thereof (water, solute, opacifier, bactericides and other standard ingredients may also be found in the stripe); and (B) 0.1 to 99%, preferably 0.1 to 70%, more preferably 0.1 to 50% by wt. of a water-in-oil emulsion stripe comprising:
  (1) About 1 to 99% of an internal aqueous phase comprising water, optional solute (0 to 30%, preferably .01 to 10% solute) and optional surfactant (0 to 30%, preferably 0.01 to 15%);
  (2) 0.5 to 99%, preferably 1 to 80% of the emulsion of an oil phase surrounding said internal aqueous phase;
  (3) about 0.1 to 20%, preferably 1 to 15% of a low HLB emulsifier (e.g., HLB under 10); and
  (4) optionally an effective amount (e.g., 0 to 40%, preferably 0.01 to 30%, preferably 0.25 to 25% of (1) a topically effective water-soluble compound (e.g., glycolic acid) found in the internal aqueous phase or (2) a "less" water soluble compound (e.g., salicylic acid) solubilized by, for example, polyalkylene glycol and/or other diluent such that it is solubilized in the internal aqueous phase.

Generally 1–40%, preferably 1–30% of this "less soluble" compound (e.g., salicylic acid) is solubilized in the diluent (e.g., PAG).

DETAILED DESCRIPTION OF THE INVENTION

The present invention relates to an at least dual chamber dispenser comprising a surfactant containing stripe on one side ((A) above) and a water-in-oil emulsion containing stripe ((B) above) on the other. The water in oil emulsion comprises an internal water phase, which may contain a water soluble benefit agent (e.g., glycolic acid) or a benefit agent solubilized in a diluent (e.g., salicylic acid in polyalkylene glycol) wherein the internal phase is emulsified in an oil phase. Each of the various components is described in greater detail below.

SURFACTANT STRIPE (Component (A))

One stripe of the dispenser of the invention is the surfactant stripe. The surfactant containing stripe is really not limited in any way and any viable surfactant system may be used although preferably this will be a "mild" surfactant system.

The surface active agent can be selected from any known surfactant suitable for topical application to the human body.

As noted, mild surfactants, i.e., surfactants which do not damage the stratum corneum, the outer layer of skin, are particularly preferred.

One preferred anionic detergent is fatty acyl isethionate of formula:

where R is an alkyl or alkenyl group of 7 to 21 carbon atoms and M is a solubilizing cation such as sodium, potassium, ammonium or substituted ammonium. Preferably at least three quarters of the RCO groups have 12 to 18 carbon atoms and may be derived from coconut, palm or a coconut/palm blend.

Another preferred anionic detergent is alkyl ether sulphate of formula:

where R is an alkyl group of 8 to 22 carbon atoms, n ranges from 0.5 to 10 especially from 1.5 to 8, and M is a solubilizing cation as before.

Other possible anionic detergents include alkyl glyceryl ether sulphate, sulphosuccinates, taurates, sarcosinates, sulphoacetates, alkyl phosphate, alkyl phosphate esters and acyl lactylate, alkyl glutamates and mixtures thereof.

Sulphosuccinates may be monoalkyl sulphosuccinates having the formula:

$R^1O_2CCH_2CH(SO_3M)CO_2M$;

and amino-MEA sulphosuccinates of the formula:

$R^1ONHCH_2CH_2O_2CCH_2CH(SO_3M)CO_2M$;

wherein $R^1$ ranges for $C_8$–$C_{20}$ alkyl, preferably $C_{12}$–$C_{15}$ alkyl and M is a solubilizing cation.

Sarcosinates are generally indicated by the formula:

$R^2CON(CH_3)CH_2CO_2M$, wherein $R^2$ ranges from $C_8$–$C_{20}$ alkyl, preferably $C_{12}$–$C_{15}$ alkyl and M is a solubilizing cation.

Taurates are generally identified by the formula:

$R^3CONR^4CH_2CH_2SO_3M$, wherein $R^3$ ranges from $C_8$–$C_{20}$ alkyl preferably $C_{12}$–$C_{15}$ alkyl, $R^4$ ranges from $C_1$–$C_4$ alkyl, and M is a solubilizing cation.

Harsh surfactants such as primary alkane sulphonate or alkyl benzene sulphonate will generally be avoided.

Suitable nonionic surface active agents include alkyl polysaccharides (e.g., alkylpolyglucoside), lactobionamides, ethylene glycol esters, glycerol monoethers, polyhydroxyamides (glucamide), primary and secondary alcohol ethoxylates, especially the $C_8$–$C_{20}$ aliphatic alcohols ethoxylated with an average of from 1 to 20 moles of ethylene oxide per mole of alcohol.

If the surface active agent comprises soap, the soap is preferably derived from materials with a $C_8$ to $C_{22}$ substantially saturated carbon chain and, preferably, is a potassium soap with a $C_{12}$ to $C_{18}$ carbon chain.

Mixtures of any of the foregoing surface active agents may also be used.

The surface active agent is preferably present at a level of from 1 to 75 wt. %, preferably 5 to 70 wt. %.

It is also preferable that the composition includes from 0.5 to 15 wt. % of a cosurfactant agent with skin mildness benefits. Suitable materials are zwitterionic detergents which have an alkyl or alkenyl group of 7 to 18 carbon atoms and comply with an overall structural formula:

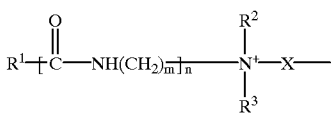

where $R^1$ is alkyl or alkenyl of 7 to 18 carbon atoms $R^2$ and $R^3$ are each independently alkyl, hydroxyalkyl or carboxyalkyl of 1 to 3 carbon atoms;

m is 2 to 4;

n is 0 or 1;

X is alkylene of 1 to 3 carbon atoms optionally substituted with hydroxyl; and

Y is —$CO_2$ or —$SO_3$.

Zwitterionic detergents within the above general formula include simple betaines of formula:

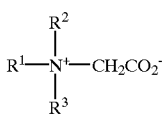

and amido betaines of formula:

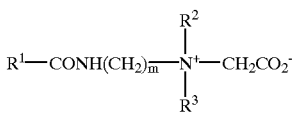

where m is 2 or 3.

In both formulae $R^1$, $R^2$ and $R^3$ are as defined previously. $R^1$ may, in particular, be a mixture of $C_{12}$ and $C_{14}$ alkyl groups derived from coconut so that at least half, preferably at least three quarters, of the group $R^1$ has 10 to 14 carbon atoms. $R^2$ and $R^3$ are preferably methyl.

A further possibility is a sulphobetaine of formula:

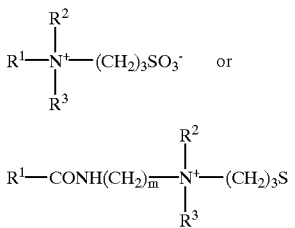

where m is 2 or 3, or variants of these in which —$(CH_2)_3SO_3$— is replaced by

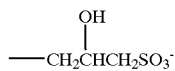

$R^1$, $R^2$ and $R^3$ in these formulae are as defined previously.

A structurant may be added to the phase comprising the surface active agent. Suitable materials include swelling clays, for example laponite; fatty acids and derivatives thereof, in particular, fatty acid monoglyceride polyglycol ethers; cross-linked polyacrylates such as Carbopol™ (polymers available from Goodrich); acrylates and copolymers thereof; polyvinylpyrrolidone and copolymers thereof; polyethylene imines; salts such as sodium chloride and ammonium sulphate; sucrose esters; gellants; and mixtures thereof.

Of the clays, particularly preferred are synthetic hectorite (laponite) clay used in conjunction with an electrolyte salt capable of causing the clay to thicken. Suitable electrolytes include alkali and alkaline earth salts such as halides, ammonium salts and sulphates.

The surface active agent phase may also comprise a thickening agent, i.e., a material which maintains the viscosity of this phase as the shear rate thereof is increased during use. Suitable materials include cross-linked polyacrylates such as Carbopol™ polymers available from Goodrich; natural gums including alginates, guar, xanthan and polysaccharide derivatives including carboxy methyl cellulose and hydroxypropyl guar; propylene glycols and propylene glycol oleates; salts such as sodium chloride and ammonium sulfate; glycerol tallowates; and mixtures thereof.

It should be appreciated that, although there is a separate benefit agent stripe (i.e., the multiple emulsion stripe $W_1$-O-$W_2$ defined by (B)), some benefit agent (e.g., hydrophobic agents such as silicone, petrolatum; or hydrophilic benefit agents or water soluble agents such as polyglycerin) may also be added to the surfactant stripe. Other components which may be used in the surfactant stripe are soluble/salts (e.g., alkali metal chloride), for example, to control viscosity; small amounts of opacifiers (preferably 0.2 to 2%), preservatives (0.2 to 2.0 wt. %), perfumes (0.5 to 2.0 wt. %) etc.

BENEFIT STRIPE (Water-In-Oil-Emulsion)

The separate benefit agent stripe is a water-in-oil emulsion stripe.

The water-in-oil emulsion composition comprises:
(1) about 1 to 99% of an internal aqueous phase containing water, 0 to 30%, preferably 0.1 to 10% solute and 0 to 30%, preferably 0.01 to 15% optional surfactant;
(2) 0.5 to 99% of an oil phase O surrounding said internal aqueous phase comprising a silicone compound, hydrocarbon compound (components may be volatile or non-volatile) or mixtures thereof;
(3) about 0.1 to 30% of a low HLB emulsifier; and
(4) optionally, a topically effective amount of (a) a water-soluble benefit agent or (b) less water soluble benefit agent dissolved in a compound which is itself soluble in water (e.g., salicylic acid in polyalkylene glycol), both (a) or (b) found in the internal water phase.

The water phase of the water-in-oil emulsion will generally comprise droplets with an internal aqueous phase containing water, optional solute (e.g., 0.01 to 10%) and a topically active compound (e.g., glycolic and/or lactic acid); and an oil phase surrounding said internal aqueous phase. Droplets may range from 0.1 to about 10 microns and may be enveloped by a membrane or film comprising oil and low HLB emulsifier.

As noted, aqueous phase comprises 1 to 99% by wt. of the water-in-oil emulsion with low HLB emulsifier separating aqueous and oil phases. The water phase may comprise water, solute and water-soluble or partially water-soluble topically active compound. It may also comprise additional active compounds and/or optional water soluble compounds providing desired esthetic or functional effect (e.g., perfume).

The aqueous phase may comprise 1–99%, preferably 10–95% of water-in-oil emulsion, more preferably 25 to 95% of emulsion.

Topically active compound may enter the water or oil phase depending on solubility (e.g., water soluble compound in water phase and oil soluble in oil phase). As noted, less water soluble compound may also be in water phase to dissolve, for example, within another compound which in turn is dissolved in water (e.g., salicylic acid in polyalkylene glycol emulsified in oil).

As used herein, the term "water soluble" means water soluble or water dispersible. A water soluble compound has a water solubility of at least 0.1 g (grams) per 100 ml (milliliters) of water and forms a true solution. A water soluble compound can be inherently water soluble or can be made water soluble by the addition of a solubilizing compound, such as a coupling agent, a co-surfactant, or a solvent. A water dispersible compound remains dispersed in water for at least the time period necessary to manufacture the primary water-in-oil emulsion, i.e., at least about one hour.

Example of compounds which may be water soluble are salicylic acid, $\alpha$-hydroxy acids (lactic acid), water soluble vitamins (e.g., vitamin B and C), water soluble antioxidants. Examples of solvents to help solubilize the less soluble compounds are alcohols such as polyalkylene glycol and ethers such as for example, PEG 15 butyl ethers, PEG 15 stearyl ether or ethylene glycol monoethyl ether.

The topically active compound therefore can be one of, or a combination of, a cosmetic compound, a medicinally active compound or any other compound that is useful upon topical application to the skin or hair. Such topically active compounds include, but are not limited to, hair conditioners (e.g., water soluble quaternary ammonium compounds, alkoxylated and nonalkoxylated fatty amines, dimethicone copolyols, cationic polymers etc.), skin conditioners (e.g., humectants such as glucose, glycerin, propylene glycol, amino acids, vitamins, amino functional silicones, etc.), hair and skin cleansers, hair fixatives, hair dyes, hair growth promoters, deodorants (e.g., organic and inorganic salts of aluminum, zirconium, zinc and mixtures thereof, skin care compounds, permanent wave compounds, hair relaxers, hair straighteners, antibacterial compounds, antifungal compounds, anti-inflammatory compounds, topical anesthetics, sunscreens and other cosmetic and medicinal topically effective compounds (e.g., antifungal, antibacterial).

Water

Sufficient water is present in the aqueous phase such that the aqueous phase comprises about 1% to about 95% by weight of the water-in-oil emulsion. Total water present in the water-in-oil emulsion composition is about 1% to about 99.9%, and typically about 25% to about 95%, by weight of the composition.

Optional

Among optional ingredients which may be included in the aqueous phase are included solutes. Among solutes which may be added are salts such as alkali metal chloride. Solute added to the internal aqueous phase may comprise 0 to 30% by wt., preferably 0.1–10% by wt.

It is also possible to add surfactant to the aqueous phase though this is added generally to the other stripe (base stripe). The surfactant can be any of the surfactants discussed in connection with the surfactant stripe.

The aqueous phase also can include optional ingredients traditionally included in topically applied compositions. These optional ingredients include, but are not limited to, dyes, fragrances, preservatives, antioxidants, detackifying agents, and similar types of compounds. As noted above, the internal phase may also include polyalkylene oxide components. These may be particularly useful for incorporating certain hydrophilic benefit agents (e.g., salicylic acid) which may otherwise be difficult to add to the aqueous phase. The optional ingredients are included in the aqueous phase of the emulsion in an amount sufficient to perform their intended function.

The Oil Phase

The oil phase may be volatile or non-volatile.

A volatile oil may comprise a volatile hydrocarbon oil which evaporates during the process of drying skin or hair, and thereby releases the internal aqueous $W_1$ phase, which includes the first topically active compound to contact the skin or hair.

In one embodiment, the oil may comprise a combination of a volatile oil and a nonvolatile oil. In this embodiment, an oil can be designed to evaporate at a preselected temperature and provide a controlled release of the first topically active compound at the pre-selected temperature. Pre-selected temperatures are those encountered during normal hair drying, provided for example by a hair dryer, or provided by a curling iron.

As previously stated, the oil also can include a water insoluble topically active compound in a sufficient amount to impart a particular functional or esthetic effect (e.g., emolliency), as long as the topically active compound does not adversely affect the emulsion composition (e.g., does not impart emulsion instability).

Volatile hydrocarbon compounds incorporated into the emulsion include, for example, isododecane and isohexadecane, i.e., PERMETHYL 99A, PERMETHYL 101A and PERMETHYL 102A, available from Presperse, Inc., South Plainfield, N.J. Other exemplary volatile hydrocarbon compounds are depicted in general structural formula (I), wherein n ranges from 2 to 5.

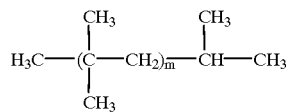

(I)

Another exemplary volatile hydrocarbon compound is ISOPAR M (a $C_{13}$–$C_{14}$ isoparaffin available from Exxon Chemical Co., Baytown, Tex.). Preferably, the volatile hydrocarbon is less than 50% unsaturated.

As previously stated, the oil also can be a nonvolatile oil. The nonvolatile oil comprises a nonvolatile silicone compound, a nonvolatile hydrocarbon, or a mixture thereof. Preferably, the nonvolatile oil comprises compounds which contain less than 50% unsaturation. The nonvolatile oil does not evaporate from the skin or hair. The first topically active compound therefore is released by rubbing the skin or hair to rupture the primary water-in-oil emulsion. A nonvolatile oil phase has a boiling point at atmospheric pressure of greater than about 250° C.

Exemplary nonvolatile silicone compounds include a polyalkyl siloxane, a polyaryl siloxane or a polyalkylaryl siloxane. Mix of these nonvolatile silicone compounds also are useful.

The nonvolatile oil also can comprise a nonvolatile hydrocarbon compound, such as mineral oil, petrolatum, sunflower seed oil, canola oil or miters thereof. Other exemplary nonvolatile hydrocarbon compounds that can be incorporated into the oil phase include, but are not limited to, a branched 1-decene oligomer, like 1-decene dimer or a polydecene.

The oil also optionally can comprise (1) an oil, such as jojoba oil, wheat germ oil or purcellin oil; or (2) a water insoluble emollient, such as, for example, an ester having at least about 10 carbon atoms, and preferably about 10 to about 32 carbon atoms.

Suitable esters include those comprising an aliphatic alcohol having about eight to about twenty carbon atoms and an aliphatic or aromatic carboxylic acid including from two to about twelve carbon atoms, or conversely, an aliphatic alcohol having two to about twelve carbon atoms with an aliphatic or aromatic carboxylic acid including about eight to about twenty carbon atoms. The ester is either straight chained or branched. Preferably, the ester has a molecular wt. of less than about 500. Suitable esters therefore include, for example, but are not limited to:

(a) aliphatic monohydric alcohol esters (e.g., isopropyl isostearate, cetyl acetate, cetyl stearate);
myristyl propionate,
isopropyl myristate,
isopropyl palmitate,
cetyl acetate,
cetyl propionate,
cetyl stearate, (b) aliphatic di- and tri-esters of polycarboxylic acids, (e.g., diisopropyl adipate);

(c) aliphatic polyhydric alcohol esters (e.g., propylene glycol dipelargonate); and (d) aliphatic esters of aromatic acids, (e.g., $C_{12}$–$C_{15}$ alcohol esters of benzoic acid).

Low HLB Emulsifier

The water-in-oil emulsion of the present invention also includes about 0.1% to about 30%, and preferably about 0.1% to about 15%, on the weight of the oil of a low HLB emulsifier.

The low HLB emulsifier may comprise a silicon-free surfactant, or a blend of silicon-free surfactants, having an HLB value of about 10 or less (i.e., an HLB value of about 0.1 to about 10), an oil-soluble silicon-based surfactant, an oil-soluble polymeric surfactant, or mixtures thereof. Preferably, the silicon-free surfactant or surfactant blend has an HLB value of about 1 to about 7. To achieve the full advantage of the present invention, the silicon-free surfactant or surfactant blend has an HLB value of about 3 to about 6. The term "oil-soluble" as used herein means a compound having a solubility of at least 0.1 g per 100 ml of oil phase to form a true solution.

The HLB value of a particular silicon-free surfactant can be found in *McCutcheon's Emulsifiers and Detergents, North American and International Editions*, MC Publishing, Glen Rock, N.J. (1993) (hereinafter *McCutcheon's*). Alternatively, the HLB value of a particular surfactant can be estimated by dividing the weight percent of oxyethylene in the surfactant by five (for surfactants including only ethoxy moieties). In addition, the HLB value of a surfactant blend can be estimated by the following formula:

HLB=(wt. % A)(HLB$_A$)+(wt. % B)(HLB$_B$), wherein wt. % A and wt. % B are the weight percent of surfactants A and B in the silicon-free surfactant blend, and HLB$_A$ and HLB$_B$ are the HLB values for surfactants A and B, respectively.

Low HLB surfactant can be a silicone-based surfactant or silicone-free surfactant.

Exemplary classes of silicon-free nonionic surfactants include, but are not limited to, polyoxyethylene ethers of fatty ($C_6$–$C_{22}$) alcohols, polyoxyethylene/polyoxypropylene ethers of fatty ($C_6$–$C_{22}$) alcohols, ethoxylated alkylphenols, polyethylene glycol ethers of methyl glucose, polyethylene glycol ethers of sorbitol, and mixtures thereof.

Exemplary silicon-free nonionic surfactants are the ethoxylated alcohols having an HLB value of about 0.1 to about 10. An especially preferred ethoxylated alcohol is laureth-1, i.e., lauryl alcohol ethoxylated with an average of one mole of ethylene oxide. Other suitable ethoxylated alcohols include laureth-2, laureth-3 and laureth-4. Numerous other nonionic surfactants having an HLB of about 0.1 to about 10 are listed in McCutcheon's at pages 229–236, incorporated herein by reference. Other exemplary silicon-free nonionic surfactants having an HLB value of about 0.1 to about 10 include, but are not limited to, the ethoxylated nonylphenols, ethoxylated octylphenols, ethoxylated dodecylphenols, ethoxylated fatty ($C_6$–$C_{22}$) alcohols having four or fewer ethylene oxide moieties, oleth-2, steareth-3, steareth-2, ceteth-2, oleth-3, and mixtures thereof.

The emulsifier can also comprise a silicon-free surfactant blend having an HLB value of about 1 to about 10. The blend is a mixture of a sufficient amount of a surfactant having allow HLB value, i.e., about 0.1 to about 10, and a sufficient amount of a surfactant having a higher HLB value, i.e., about 1 to greater than about 10, such that the surfactant blend has an HLB value of about 1 to about 10. Exemplary, but non-limiting, nonionic surfactants having a high HLB value are listed in McCutcheon's at pages 236–246, incorporated herein by reference.

A preferred silicone-free surfactant is PEG-30 dipolyhydroxystearate.

An exemplary oil-soluble silicon-based surfactant is a dimethicone copolyol, which is a dimethylsiloxane polymer having polyoxyethylene and/or polyoxypropylene side chains, such as DOW CORNING 322C FORMULATION AID, available from Dow Corning Co., Midland, Mich. The dimethicone copolyol has about 15 or fewer ethylene oxide and/or propylene oxide monomer units, in total, in the side chains. Dimethicone copolyols conventionally are used in conjunction with silicones because the silicon-containing surfactants are extremely soluble in a volatile or a nonvolatile silicone compound, are extremely insoluble in water, and have a low skin irritancy potential.

Another exemplary, but non-limiting, oil-soluble, silicon-based surfactant is an alkyl dimethicone copolyol, such as cetyl dimethicone copolyol available commercially as ABIL (R) EM 90 from Goldschmidt Chemical Corporation, Hopewell, Va. The alkyl dimethicone copolyols have the structure:

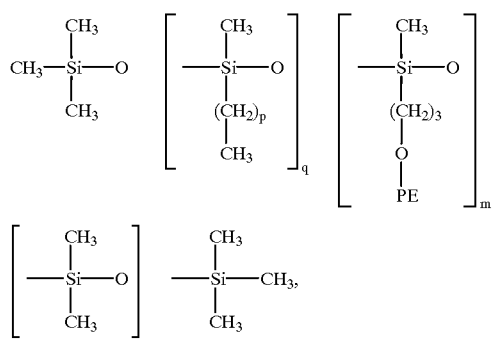

wherein:
p is a numeral from 7 through 17;
q is a numeral from 1 through 100;
m is a numeral from 1 through 40;
n is a numeral from 0 through 200; and
PE is $(C_2H_4O)_a(C_3H_6O)_b$-H having a molecular weight of about 250 to about 2000, wherein a and b are selected such that the weight ratio of $C_2H_4O/C_3H_6O$ is from 100/0 to 20/80.

The emulsifier may also be an oil-soluble polymeric surfactant. Polymeric surfactants capable of forming water-in-oil emulsions completely cover the surface of the water droplet, are firmly anchored at the oil-water interface, the external oil phase is a good solvent for the stabilizing portion of the polymeric surfactant, and the thickness of the polymer layer on the oil side of the interface is sufficient to ensure stability. These surfactants may include ethoxy, propoxy and/or similar alkylene oxide monomer units, e.g., butoxy. The oil-soluble polymeric surfactants act as surfactants and are not physically or chemically cross-linked in solution. The oil-soluble polymeric surfactants therefore are differentiated from polymeric gelling agents such as polyacrylic acid or polymethacrylic acid.

Accordingly, exemplary oil-soluble polymeric surfactants include, but are not limited to, polyoxyethylene-polyoxypropylene block copolymers, and similar polyoxyalkylene block copolymers. The oil-soluble block copolymers typically have less than about 20% by weight of ethylene oxide. Specific non-limiting oil-soluble polymeric surfactants include Poloxamer 101, Poloxamer 105, PPG-2-Buteth-3, PPG-3-Butech-5, PPG-5-Butech-7, PPG-7-Butech-10, PPG-9-Buteth-12, PPG-12-Buteth-16, PPG-15-Buteth-20, PPG-20-Buteth-30, PPG-24-Buteth-27, PPG-28-Buteth-35, and PEG-15 Butanediol. Other useful oil-soluble polymeric surfactants are polyamines, i.e., polyoxyethylene-polyoxypropylene block copolymers of ethylene diamine, having less than about 40% by weight ethylene oxide.

In accordance with an important feature of the present invention, the hydrophobic moiety of a silicon-free surfactant, silicon-containing surfactant or polymeric surfactant is sufficiently soluble in the oil phase such that a sufficient amount of the surfactant is present in the oil phase to stabilize the primary $W_1/O$ emulsion. In one embodiment when the oil phase comprises a silicone compound, the surfactant phase comprises either a silicon-based surfactant, a silicon-free surfactant having a hydrophobic moiety preferably containing about ten to about fourteen carbon atoms, an oil-soluble polymeric surfactant, or a mixture thereof. If the hydrophobic moiety of the silicon-free surfactant is saturated and includes more than about 14 carbon atoms, the silicon-free surfactant is insoluble in the silicone phase and the water-in-oil emulsion is unstable. If the hydrophobic moiety includes less than about 10 carbon atoms, the emulsion has a tendency to coalesce i.e., the emulsion droplets fuse to form large droplets. The amount of surfactant phase necessary to provide an emulsion of desired $W_1/O$ droplet diameter varies with the amount of aqueous phase in the primary emulsion and is easily determined by those skilled in the art.

One particularly preferred emulsifier is cetyl dimethicone copolyol.

According to the invention, the benefit agent stripe (with water-in-oil emulsion) and surface active agent stripe are separate but combinedly dispensable from a packaging means and typically a single packaging means. Such a packaging means includes those systems which comprise two separate compartments. Ensuring that the surface active agent and benefit agent are separate can be achieved in a variety of ways. Packaging of the composition such that the surface active agent and benefit agent are presented in separate compartments or in separate domains within the packaging; including encapsulation of the benefit agent; and by processing of the composition by coextrusion to produce a striped product in which individual stripes contain either the surface active agent or benefit agent.

Compositions of the invention may be formulated as products for washing the skin, for example, bath or shear gels, hand washing compositions or facial washing liquids; pre- and post-shaving products; rinse-off, wipe-off and leave-on skin care products; products for washing the hair and for dental use.

The compositions of the invention will generally be pourable liquids or semi-liquids, e.g., pastes and will have a viscosity in the range of 250 to 100,000 mPas measured at a shear rate 10 $s^{-1}$ and 25° C. in a Haake rotoviscometer RV20.

When the product is formulated as a shower gel the viscosity will generally be in the range 200 to 15000 mPas, preferably 500 to 15,000 measured at a shear rate $10s^{-1}$ and 25° C.

When the product is formulated as a facial wash product the viscosity will generally be in the range 3000 to 100,000 mPas measured at a shear rate $10s^{-1}$ and 25° C.

Other typical components of such compositions include opacifiers, preferably 0.2 to 2.0 wt. %; preservatives, preferably 0.2 to 2.0 wt. % and perfumes, preferably 0.5 to 2.0 wt. %.

Except in the operating and comparative examples, or where otherwise explicitly indicated, all numbers in this description indicating amounts or ratios of materials or conditions or reaction, physical properties of materials and/ or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

All percentages used, unless indicated otherwise, are intended to be percentages by weight.

Glycolic Acid and Sodium Glycolate Deposition Protocol

Procedure for Analyzing the Deposition of Glycolic Acid and Sodium Glycolate from Cleansers by Gas Chromatography (GC)/Liquid Chromatography (LC)

Test Procedure (Pigskin):

Fresh Piglet skin (4–5 weeks old, male, white, no nipples and shaved) is used for the deposition studies. The skin is cut into ~12 cm×5 cm pieces which are stretched and pinned onto a support. The surface of the skin is wetted with 250 mls water and 1 gram of cleanser is applied to the wet surface (0.5 gram benefit stripe and 0.5 gram of surfactant phase). The skin is then washed by hand for 30–60 seconds, rinsed three times with 250 mls aliquots of water and patted dry with Kimwipe paper towel. A glass/plastic cylinder 3.3 cm in diameter is then placed in close contact with the skin surface and the skin is extracted three times with 3 ml aliquots of organic solvent (ethanol, acetone or tetrahydrofuran) followed by another three times with 3 ml aliquots of distilled water. The organic solvent extracts are combined. The same is done for the water extracts. (The water and/or organic solvent extractions can be repeated several times depending on the concentration of sodium glycolate, glycolic acid or other tested benefit agent on the pigskin). In the case of glycolic acid and sodium glycoside, for example, the organic extract will contain the glycolic acid and the water will contain the sodium glycolate.

Three sites are extracted on each of three pieces of skin for each formulation. The concentration of, for example, the sodium glycolate and the glycolic acid on the skin (in $\mu g/cm^2$) is determined by comparison with standard solutions on the Gas Chromatography and/or Liquid Chromotography using analytic procedure below.

Analytical Procedure

Apparatus 1:

A suitable Gas Chromatography (HP 5890 series II perhaps)

Sil-prep from Alitech (part #18013)

Gas Chromatography Setting:

Detector: Flame Ionization Detector

Column: HP-1 100%-Polydimethylsiloxane, Column length 25.9 m, Inside diameter 0.2 mm, Film thickness 0.33 mm Injector Volume 4.0 $\mu L$–5.0 $\mu L$ Gases: Helium (carrier), Hydrogen and Air (Flame)

Flow rate:

Total flow rate:

Detector temp.: 250° C.

Injector temp.: 250° C.

Oven temperature: Set point 50 C., limit 300 C.

Run time: 14.6 minutes

Oven Temperature Profile:

Initial temp.: 50 C.

Initial time: 0.0

Rate: 25 C/minute

Final temp.: 290 C.

Final time: 14.6 minutes

Standards:

Solutions at 4000, 2000, 1000, 500, 250, 125, 62.5, 31.3, 15.6, 7.8 $\mu g/ml$ are prepared. Glycolic acid in organic solvent. Sodium glycolate in water.

Procedure

1. Place 1 ml of sample into a vial;
2. Completely remove solvent from sample using a vacuum;
3. Add one ampoule of sil-prep reagent to sample;
4. Sonicate or stir sample for ~15 minutes;
5. Inject silted sample into gas chromatograph.

Using procedures above, measure the area response of the standards. Calculate a regression line for the standards, including the zero point, using the measured area responses.

Measure the area response of the extract samples. Using the regression line calculate the unknown concentration of the extract.

Apparatus 2:

A suitable Liquid Chromatography (HP)

Liquid Chromatography Settings:

Detector: UV Detector

Column: Phenomenex LUNA 5 $\mu$ C.18(2)

Injector volume: 5.0 $\mu L$–50.0 $\mu L$

Mobil phase: 97% 20 nM Potassium Phosphate @ pH 2.3:3% Methanol

Flow rate: 0.7 ml/minute

Temperature: 25 C.

Run time: 30 minutes

Standards:

Solutions at 4000, 2000, 1000, 500, 250, 125, 62.5, 31.3, 15.6, 7.8 µg/ml are prepared.

Procedure

1. Place 1 ml of sample into a vial;
2. Completely remove solvent from sample using a vacuum;
3. Add one milliliter of mobile phase to sample;
4. Inject sample into LC.

Using procedures above, measure the area response of the standards. Calculate a regression line for the standards, including the zero point, using the measured area responses.

Measure the area response of the extract samples. Using the regression line calculate the unknown concentration of the extract.

EXAMPLES

Example 1

Preparation of Water-Oil Emulsion (Benefit Agent Stripe)

Ingredients (1) Glycolic Acid Solution (44% active @ pH 4) (glycolic acid would be used as the benefit agent in internal aqueous phase);
(2) Petrolatum (oil phase);
(3) Abil EM90 Goldschmidt (cetyl dimethicone copolyol low HLB emulsifier);
(4) Borage seed oil;
(5) Glydant II (preservative)

Preparation

In a beaker, petrolatum (oil phase), EM90 (emulsifier) and borage seed oil were added. Petrolatum can be any of different petrolatums including Fuchs Silkolene 910, Penreco's snow white, lily white, blond, etc. Other oils which can be used as oil phase include Guerbet® esters such as, for example, octyidodecyl recionoleate; silicone emulsions; mixtures of petrolatum and silicone, etc. Other oils which can be used as oil phase include Guerbet® esters such as, for example, octyldodecyl recionoleate; silicone emulsions; mixtures of petrolatum and silicone, etc.

Contents were heated to ~65–70 C. (allowing petrolatum or oil to melt). Contents were stirred at approximately 800–900 rpms. While stirring, glycolic acid solution (premix of Example 2) (or salicylic acid in PEG if this was the benefit agent in aqueous phase) was added dropwise at pH 4 while stirring at 700 RPM. After addition of glycolic acid (or other benefit agent), mixture was homogenized at 10,000 rpm for 10–15 minutes, mixture was cooled to 50° C. and Glydant II (preservative) was added.

NaOH was in final stripe because it was part of the glycolic acid premix as made in Example 2.

Example 2

Preparation of Glycolic Acid Premix Used to Prepare Benefit Agent Stripe

Ingredients (1) Glycolic Acid Solution (44% active @ pH 4);
(2) Water;
(3) NaOH @ 50%;
(4) Glycolic Acid @ 99.0%;
(5) Carbomer (optional); helps to thicken and may aid deposition.

Preparation

Water was added to a beaker. Glycolic acid was added and stirred until glycolic acid had dissolved. Glycolic acid solution was cooled to 0 degrees C. NaOH was slowly added (drop-wise). After addition of NaOH, ingredients were cooled to room temperature. Carbomer was optionally added to solution slowly, stirring rapidly until Carbomer was fully dispersed. Solution became viscous.

Example 3

Following is an example of a "Base" stripe which was prepared to be used as surfactant stripe phase ((A)):

| Ingredient | % By Wt. |
|---|---|
| Acyl Isethionate | 1–10% |
| Betaine | 5–15% |
| Sodium Lauryl Ether Sulfate | 2–5% |
| Nonionic | 0–8% |
| NaOH | 0–2% |
| Lytron 621 (Opacifier) | 0–2% |
| Antil 141 (Thickener) | 0–3% |
| Preservative (e.g., Glydant II) | 0–2% |
| Water and optional fragrance | To balance |

Example 4

(Dual Composition)

The following water-in-oil (Petrolatum) benefit agent stripe (Stripe B) and base (Central Base, Stripe A) were prepared:

Stripe A—Base

| Ingredient | % Active |
|---|---|
| Cocamidopropyl betaine | 0–5 |
| Sodium cocoyl isethionate | 6–8 |
| LAS | 6–9 |
| Cationic polymer (Jaguar C13S ex Rhone Poulenc) | 1.5 |
| Glycerin | 0–20 |
| Coco monoethanolamide | 0–10 |
| Thickeners | 0–1.0 |
| Fragrance, minors | 0–1.0 |
| Water | To balance |

LAS = linear alkyl benzene sulphonate

Stripe B—Benefit Agent Stripe (Water-in-Oil Benefit Stripe)

| Ingredient | % Active |
|---|---|
| Petrolatum | 36.6 |
| Glycerin | 10.0 |
| Cetyl dimethicone copolyol | 1–5.0 |
| Borage seed oil | 1.0 |
| Hydroxyacetic acid (glycolic acid) | 20.0* |
| Ceteth-20 (NI Surfactant) | 0.1 |
| Carbopol | 1.0 |
| Sodium hydroxide | 5–6 |
| DMDM Hydantoin | 0.2 |
| Water | To balance |

*In general in both base and stripe phases, levels come out as half of the amount when dispersed. Thus, 20% glycolic in benefit agent stripe is dispersed as 10% glycolic when out of the container.

Comparative A (Oil-In-Water Benefit Stripe)

The following dual stripe composition was also prepared but, in contrast to Example 4, the benefit agent stripe was not water-in-oil emulsion with 10% glycolic acid but an oil-in-water emulsion with 10% glycolic. The base and benefit stripes are as follows:

Stripe A—Base

| Ingredient | % Active |
|---|---|
| Cocamidopropyl betaine | 10.0 |
| Sodium cocoyl isethionate | 3.0 |
| Sodium laureth sulfate | 2.0 |
| Thickener | 0.0–5 |
| Fragrance, minors | 0–1.0 |
| Water | To balance |

Stripe B—Benefit Agent (Oil-In Water Emulsion)

| Ingredient | % Active |
|---|---|
| Petrolatum | 36.0 |
| Borage seed oil | 1.0 |
| Hydroxyacetic acid (glycolic acid) | 20.0 |
| Ceteth 20 (NI Surfactant) | 0.1 |
| Carbopol | 1.0 |
| Sodium hydroxide | 5–6 |
| DMDM Hydantoin | 0.2 |
| Water | To balance |

Benefit Agent in Comparativecontains no glycerin.

Comparative B (Single Cleanser)

The following single cleanser system was prepared and was used in Example 5 set forth below:

| Ingredient | % Active |
|---|---|
| Cocamidopropyl betaine | 10.0 |
| Sodium acyl isethionate | 3.0 |
| Sodium laureth sulfate | 2.0 |
| Borage seed oil | 1.0 |
| Hydroxyacetic acid (glycolic acid) | 10.0 |
| Sodium hydroxide | 5–6 |
| DMDM Hydantoin | 0.36 |
| Water | To balance |

Example 5

Using the composition of Example 4 and of the Comparative A (dual cleanser where glycolic acid is directly in water phase), these were compared for deposition results using protocol set forth previously and the results are set forth below:

| O/W Composition | W/O Composition |
|---|---|
| 32 μg/cm² | 432 μg/cm² |

These paragraphs clearly show that a much greater amount of glycolic acid was deposited from W/O emulsion system than from O/W emulsion system.

Example 6

Applicants also compared deposition from water-in-oil emulsion system from dual stripe cleanser system compared to deposition from a single stripe cleanser as set forth in Comparative B. These results are as follows:

| Single Stripe | Dual Stripe with W/O Emulsion in Benefit Stripe |
|---|---|
| 5.0 μg/cm² | 432 μg/cm² |

These paragraphs clearly show that a much greater amount of glycolic acid was deposited from W/O emulsion system than from single system.

Example 7

Benefit Stripe with Petrolatum and Salicylic Acid (2%)

A dual chamber composition was prepared having a surfactant base stripe as set forth in "A" below and benefit stripe asset forth in "B" below:

A—Surfactant Base Stripe

| Ingredient | % Active |
|---|---|
| Cocoamidopropyl betaine | 10 |
| Sodium cocoyl isethionate | 3 |
| Sodium laureth sulfate | 2 |
| Propylene glycol & PEG 55 Propylene glycol oleate | 0.5 |
| Opacifier | 0.34 |
| Perfume/fragrance | 0.2 |
| DMDM Hydantoin | 0.2 |
| Water | To balance |

B—Petrolatum and Salicylic Acid Benefit Stripe

This is example of salicylic acid in PEG as benefit agent in oil (petrolatum) stripe.

| Ingredient | % Active |
|---|---|
| Silkolene 910 petrolatum | 48.3 |
| Cetyl dimethicone copolyol | 4.7 |
| Salicylic acid | 4.0 |
| Polyethylene glycol* | 10.0 |
| NaOH | 5.46 |
| Preservative | 0.2 |
| Water | To balance |

*PEG 300

Example 8

In order to show enhanced deposition of salicylic acid benefit stripe (Example 7), applicants compared dual stripe of Example 7 to a dual stripe composition with water-oil-water emulsion. The water-oil-water stripe and benefit stripe of comparative are set forth below:

Surfactant

| Ingredient | % Active |
|---|---|
| Betaine | 10.0 |
| Sodium Cocoyl Isethionate | 3.0 |
| Sodium Laureth Sulfate | 2.0 |
| Propylene Glycol and PEG-55 Propylene Glycol Oleate | 0.5 |
| Styrene Acrylate Copolymer | 0.34 |
| Perfume/Fragrance | 0.2 |

-continued

| Ingredient | % Active |
|---|---|
| DMDM Hydantoin | 0.2 |
| Water | 83.76 |

Benefit Stripe

| Ingredient | % Active |
|---|---|
| Silkolene 910 Petrolatum | 36.0 |
| Cetyl Dimethicone Copolyol | 3.6 |
| Salicylic Acid | 4.0 |
| Polyethylene Glycol | 10.0 |
| Ceteth-20 | 0.1 |
| Carbopol Thickener | 1.0 |
| Sodium Hydroxide | 5.6 |
| Water | 39.50 |
| DMDM Hydantoin | 0.2 |

Deposition results of use of WOW emulsion compared to WO emulsion of Example 7 are set forth below:

| WOW Emulsion | Example 7 |
|---|---|
| Deposition: 3 g/cm$^2$ | 171 g/cm$^2$ |

This example clearly shows benefit of W/O emulsion relative to WOW emulsion.

Example 9

Dual Chamber with Different Base Stripe ("A") and Benefit Stripe

A—Surfactant Base Stripe

| Ingredient | % Active |
|---|---|
| Linear alkyl benzene sulphonate (LAS) | 7.5 |
| Acyl isethionate | 7.5 |
| Cocomonoethanolamide | 5.0 |
| Glycerin | 10.0 |
| Guar hydroxypropyl trimonium chloride | 1.0 |
| Opacifier | 0.34 |
| Fragrances, preservative | 0.4 |
| Water | To balance |

B—Petrolatum & Salicylic Acid Base Stripe

| Ingredient | % Active |
|---|---|
| Cream white petrolatum | 48.3 |
| Cetyl dimethicone copolyol | 4.7 |
| Salicylic acid | 4.0 |
| PEG | 10.0 |
| NaOH | 5.46 |
| Preservative | 0.2 |
| DMDM Hydantoin | 0.2 |
| Water | To balance |

This shows use of dual stripe with benefit agent stripe using slightly different petrolatum and with slightly different surfactant base "A".

Example 10

The following are examples of two other petrolatum benefit stripes which may be used (as stripe "B") with any of the surfactant stripes (stripe "A") of the invention.

Benefit Stripe with 10% L-Lactic Acid and 2% Salicylic Acid

Stripe B—Benefit Agent (Oil-In Water Emulsion)

| Ingredient | % Active |
|---|---|
| Petrolatum | 30.0 |
| PEG 300 | 10.0 |
| Borage seed oil | 1.5 |
| L-Lactic acid | 20.0 |
| Cetyl dimethicone copolyol | 3.0 |
| Salicylic acid | 4.0 |
| Preservative | 0.2 |
| NaOH | 4.5 |
| Water | To balance |

Benefit Stripe with 8.5% Glycolic Acid & 7.5% Menthyl Lactate

| Ingredient | % Active |
|---|---|
| Petrolatum | 40.0 |
| Cetyl dimethicone copolyol | 4.0 |
| Borage seed oil | 1.5 |
| L-Menthyl lactate | 15.0 |
| Hydroxyacetic acid (Glycolic) | 17.2 |
| Preservative | 0.2 |
| NaOH | 4.68 |
| Water | To balance |

This example clearly shows that a variety of emollients/benefit agent can be used in the benefit stripe of the invention.

What is claimed is:

1. An aqueous liquid cleansing and moisturizing composition comprising:
   (A) 10 to 99.9% by wt. of a surfactant stripe comprising 1 to 75% by wt. of a surface active agent selected from the group consisting of anionic, nonionic, zwitterionic and cationic surface active agents, soap and mixtures thereof; and
   (B) 0.1 to 99% by wt. of a benefit agent stripe comprising a water-in-oil emulsion where said emulsion comprises:
      (1) 1 to 99% of an internal aqueous phase containing water, optional solute and optional surfactant;
      (2) 0.5 to 99% at an oil phase surrounding said internal aqueous phase;
      (3) 0.1 to 20% of a surfactant emulsifier having HLB of below 10; and
      (4) optionally, a topically effective amount of a water-soluble or partially water-soluble benefit agent in the internal aqueous phase.

2. A composition according to claim 1, wherein surfactant of (A) comprises 5 to 70% of stripe.

3. A composition according to claim 1, wherein benefit agent is added to surfactant Stripe (A).

4. A composition according to claim 1, wherein water-in-oil emulsion comprises 0.1 to 10% by wt. solute.

5. A composition according to claim 1, wherein oil phase of water-in-oil emulsion encapsulates internal aqueous phase to form droplets of about 5 to about 1000 μ.

6. A composition according to claim 1, wherein emulsifier having HLB below 10 comprises 0.1 to 15% of oil phase.

7. A composition according to claim 6, wherein emulsifier is a dimethicone copolyol.

8. A composition according to claim 1, wherein topically effective compounds of water-in-oil emulsion comprises glycolic acid.

9. A composition according to claim 1, where topically effective compound comprises salicylic acid.

10. A composition according to claim 1, wherein topically effective compound comprises lactic acid.

11. A composition according to claim 1, wherein topically effective compound comprises lactic acid and salicylic acid.

12. A composition according to claim 1, wherein topically effective compound comprises alkyl ester of lactic acid.

13. A composition according to claim 1, wherein topically effective compound comprises glycolic acid and alkyl ester of lactic acid.

14. A composition according to claim 1 wherein external aqueous phase comprises 20–95% water-in-oil emulsion.

* * * * *